United States Patent
Cass et al.

(10) Patent No.: US 11,458,300 B2
(45) Date of Patent: Oct. 4, 2022

(54) OVERMOLDED SEGMENTED ELECTRODE

(71) Applicant: Heraeus Medical Components LLC, St. Paul, MN (US)

(72) Inventors: Robert R. Cass, Minneapolis, MN (US); Paul Noffke, St. Paul, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 398 days.

(21) Appl. No.: 16/718,368

(22) Filed: Dec. 18, 2019

(65) Prior Publication Data

US 2020/0206494 A1 Jul. 2, 2020

Related U.S. Application Data

(60) Provisional application No. 62/785,968, filed on Dec. 28, 2018.

(51) Int. Cl.
| | | |
|---|---|---|
| A61N 1/05 | (2006.01) | |
| A61N 1/08 | (2006.01) | |
| B23P 13/00 | (2006.01) | |
| B29C 70/72 | (2006.01) | |
| H01B 13/00 | (2006.01) | |
| H01L 21/56 | (2006.01) | |

(Continued)

(52) U.S. Cl.
CPC ............. *A61N 1/0534* (2013.01); *A61N 1/05* (2013.01); *A61N 1/08* (2013.01); *B23P 13/00* (2013.01); *B29C 70/72* (2013.01); *H01B 13/00* (2013.01); *H01L 21/56* (2013.01); *H01L 21/64* (2013.01); *H05K 13/00* (2013.01); *A61B 2562/227* (2013.01); *A61N 1/0551* (2013.01); *A61N 1/3605* (2013.01); *B29L 2031/753* (2013.01)

(58) Field of Classification Search
CPC .. A61B 2562/227; A61N 1/05; A61N 1/0534; A61N 1/0551; A61N 1/08; A61N 1/3605; B23P 13/00; B29C 70/72; B29L 2031/753; H01B 13/00; H01L 21/56; H01L 21/64; H05K 13/00
See application file for complete search history.

(56) References Cited

U.S. PATENT DOCUMENTS

| | | |
|---|---|---|
| 3,939,843 A | 2/1976 | Smyth |
| 5,000,194 A | 3/1991 | van den Honert et al. |

(Continued)

FOREIGN PATENT DOCUMENTS

| | | |
|---|---|---|
| EP | 2144665 | 1/2010 |
| EP | 2519307 | 11/2012 |

(Continued)

*Primary Examiner* — George Manuel
(74) *Attorney, Agent, or Firm* — Dicke, Billig & Czaja, PLLC (57) ABSTRACT

One aspect is forming a medical lead for implantation. The method includes forming a plurality of non-ground electrodes, at least one non-ground electrode having a plurality of segments. Overmold portions are formed for the at least one of the plurality of non-ground electrodes, including keys and tabs. One of a plurality of conductors is attached to one segment of the at least one non-ground electrode using the keys and tabs. The non-ground electrodes and plurality of conductors are assembled into electrode assembly and the overmold portions are reflowed. The reflowed electrode assembly is then ground to form the medical lead.

9 Claims, 11 Drawing Sheets

(51) Int. Cl.
  *H01L 21/64* (2006.01)
  *H05K 13/00* (2006.01)
  *A61N 1/36* (2006.01)
  *B29L 31/00* (2006.01)

(56) References Cited

U.S. PATENT DOCUMENTS

| | | |
|---|---|---|
| 5,376,206 A | 12/1994 | Maurer et al. |
| 5,843,148 A | 12/1998 | Gijsbers et al. |
| 6,185,465 B1 | 2/2001 | Mo et al. |
| 6,201,981 B1 | 3/2001 | Yarita |
| 6,249,708 B1 | 6/2001 | Nelson et al. |
| 6,256,542 B1 | 7/2001 | Marshall et al. |
| 6,456,863 B1 | 9/2002 | Levin et al. |
| 6,595,991 B2 | 7/2003 | Toellner et al. |
| 6,600,956 B2 | 7/2003 | Maschino et al. |
| 6,925,334 B1 | 8/2005 | Salys |
| 6,999,821 B2 | 2/2006 | Jenney et al. |
| 7,047,081 B2 | 5/2006 | Kuzma |
| 7,212,867 B2 | 5/2007 | Van Venrooij et al. |
| 7,212,868 B2 | 5/2007 | McAuliffe et al. |
| 7,310,873 B2 | 12/2007 | Pardo et al. |
| 7,437,197 B2 | 10/2008 | Harris et al. |
| 7,551,967 B1 | 6/2009 | Karicherla et al. |
| 7,654,843 B2 | 2/2010 | Olson et al. |
| 7,668,601 B2 | 2/2010 | Hegland et al. |
| 7,717,754 B2 | 5/2010 | Ries et al. |
| 7,761,985 B2 | 7/2010 | Hegland et al. |
| 7,798,864 B2 | 9/2010 | Barker et al. |
| 7,822,476 B2 | 10/2010 | Bartels et al. |
| 7,917,213 B2 | 3/2011 | Bulkes et al. |
| 7,996,092 B2 | 8/2011 | Mrva et al. |
| 8,036,755 B2 | 10/2011 | Franz |
| 8,046,909 B2 | 11/2011 | Dye et al. |
| 8,225,504 B2 | 7/2012 | Dye et al. |
| 8,244,372 B1 | 8/2012 | Zhulati et al. |
| 8,250,754 B2 | 8/2012 | Seifert |
| 8,250,755 B2 | 8/2012 | Dye |
| 8,271,100 B2 | 9/2012 | Boser et al. |
| 8,280,528 B2 | 10/2012 | Kuzma et al. |
| 8,316,537 B2 | 11/2012 | Black et al. |
| 8,320,988 B2 | 11/2012 | Axelgaard |
| 8,322,026 B2 | 12/2012 | McDonald |
| 8,340,759 B2 | 12/2012 | McIntyre et al. |
| 8,340,783 B2 | 12/2012 | Sommer et al. |
| 8,442,658 B2 | 5/2013 | Li |
| 8,478,423 B2 | 7/2013 | McDonald et al. |
| 8,515,557 B2 | 8/2013 | Capcelea et al. |
| 8,560,074 B2 | 10/2013 | McDonald |
| 8,571,685 B2 | 10/2013 | Daglow et al. |
| 8,583,237 B2 | 11/2013 | Bedenbaugh |
| 8,588,939 B2 | 11/2013 | Conger |
| RE44,667 E | 12/2013 | Rock |
| 8,639,355 B2 | 1/2014 | Soltis |
| 8,646,172 B2 | 2/2014 | Kuzma et al. |
| 8,660,663 B2 | 2/2014 | Wolf et al. |
| 8,666,494 B2 | 3/2014 | Schramm et al. |
| 8,671,566 B2 | 3/2014 | Black et al. |
| 8,712,542 B2 | 4/2014 | McMorrow et al. |
| 8,712,547 B2 | 4/2014 | Whitehurst et al. |
| 8,739,403 B2 | 6/2014 | Hegland et al. |
| 8,784,714 B2 | 7/2014 | Horrisberger et al. |
| 8,816,711 B2 | 8/2014 | Lyders et al. |
| 8,874,232 B2 | 10/2014 | Chen |
| 8,892,214 B2 | 11/2014 | Bonde et al. |
| 8,897,890 B2 | 11/2014 | Alexander et al. |
| 8,923,982 B2 | 12/2014 | Howard |
| 8,925,191 B2 | 1/2015 | Swanson et al. |
| 8,966,745 B2 | 3/2015 | Barker |
| 8,972,995 B2 | 3/2015 | Srinivasan et al. |
| 9,008,797 B2 | 4/2015 | Fan et al. |
| 9,054,436 B2 | 6/2015 | Swanson et al. |
| 9,089,689 B2 | 7/2015 | Govea |
| 9,101,755 B2 | 8/2015 | Pianca |
| 9,101,776 B2 | 8/2015 | Hughes |
| 9,106,004 B2 | 8/2015 | Olson et al. |
| 9,138,576 B2 | 9/2015 | Klardie et al. |
| 9,162,053 B2 | 10/2015 | Schulte et al. |
| 9,192,758 B2 | 11/2015 | Alexander et al. |
| 9,227,049 B2 | 1/2016 | Regnier et al. |
| 9,248,276 B2 | 2/2016 | Pianca et al. |
| 9,278,223 B2 | 3/2016 | Kast et al. |
| 9,289,596 B2 | 3/2016 | Leven |
| 9,364,659 B1 | 6/2016 | Rao |
| 9,368,925 B2 | 6/2016 | Lim et al. |
| 9,370,653 B2 | 6/2016 | Sefkow et al. |
| 9,375,563 B2 | 6/2016 | Govea |
| 9,421,360 B2 | 8/2016 | Conger et al. |
| 9,427,574 B2 | 8/2016 | Lee et al. |
| 9,474,894 B2 | 10/2016 | Mercanzini et al. |
| 9,545,207 B2 | 1/2017 | Clark et al. |
| 9,555,234 B2 | 1/2017 | Duijsens et al. |
| 9,561,362 B2 | 2/2017 | Malinowski |
| 9,566,747 B2 | 2/2017 | Romero et al. |
| 9,604,049 B2 | 3/2017 | Lim et al. |
| 9,615,760 B2 | 4/2017 | Lichtenstein |
| 9,622,678 B2 | 4/2017 | Bozzarelli |
| 9,737,704 B2 | 8/2017 | Wahlstrand et al. |
| 9,742,130 B2 | 8/2017 | Glynn et al. |
| 9,757,555 B2 | 9/2017 | Novotny et al. |
| 9,775,988 B2 | 10/2017 | Govea et al. |
| 9,795,779 B2 | 10/2017 | Pianca et al. |
| 9,800,010 B2 | 10/2017 | Farr et al. |
| 9,844,661 B2 | 12/2017 | Franz et al. |
| 9,878,148 B2 | 1/2018 | Leven et al. |
| 9,913,974 B2 | 3/2018 | Pianca et al. |
| 9,950,158 B2 | 4/2018 | True et al. |
| 9,962,539 B2 | 5/2018 | Seeley et al. |
| 9,993,637 B2 | 6/2018 | Leven |
| 10,058,698 B2 | 8/2018 | Xu et al. |
| 10,076,657 B2 | 9/2018 | Oster et al. |
| 10,112,044 B2 | 10/2018 | Skubitz et al. |
| 10,124,161 B2 | 11/2018 | Barker |
| 10,218,133 B2 | 2/2019 | Hanson et al. |
| 2005/0038489 A1 | 2/2005 | Grill |
| 2007/0005053 A1 | 1/2007 | Dando |
| 2007/0255320 A1 | 11/2007 | Inman et al. |
| 2010/0004525 A1 | 1/2010 | Osypka |
| 2010/0016935 A1 | 1/2010 | Strandberg et al. |
| 2010/0137964 A1 | 6/2010 | Siefert et al. |
| 2010/0210146 A1 | 8/2010 | Jang et al. |
| 2010/0331942 A1 | 12/2010 | Cholette et al. |
| 2011/0047795 A1 | 3/2011 | Turner et al. |
| 2011/0077699 A1 | 3/2011 | Swanson et al. |
| 2011/0130818 A1 | 6/2011 | Chen |
| 2014/0107455 A1 | 4/2014 | Regnier et al. |
| 2014/0358174 A1 | 12/2014 | Thenuwara et al. |
| 2015/0074995 A1 | 3/2015 | Patil et al. |
| 2015/0080995 A1* | 3/2015 | Seeley ................ A61N 1/05 607/116 |
| 2015/0142090 A1 | 5/2015 | Duijsens et al. |
| 2015/0202432 A1 | 7/2015 | Somogyi et al. |
| 2016/0100768 A1 | 4/2016 | Someya et al. |
| 2016/0121106 A1 | 5/2016 | Marshall et al. |
| 2017/0189674 A1 | 7/2017 | Camps et al. |
| 2017/0266451 A1 | 9/2017 | Lim et al. |
| 2017/0312500 A1 | 11/2017 | Shoberg et al. |
| 2018/0042506 A1 | 2/2018 | Locke et al. |
| 2019/0060634 A1 | 2/2019 | Skubitz et al. |
| 2019/0067719 A1 | 2/2019 | Rock |

FOREIGN PATENT DOCUMENTS

| | | |
|---|---|---|
| EP | 2846681 | 3/2015 |
| EP | 3113833 | 1/2017 |
| WO | 2008/133616 | 11/2008 |
| WO | 2011/081778 | 7/2011 |
| WO | 2018/089168 | 5/2018 |
| WO | 2018/102695 | 6/2018 |

* cited by examiner

OVERMOLDED SEGMENTED ELECTRODE

CROSS-REFERENCE TO RELATED APPLICATION

This application is a non-provisional of U.S. Patent Application Ser. No. 62/785,968, filed Dec. 28, 2018, which is incorporated herein by reference.

TECHNICAL FIELD

One aspect relates to overmolded electrodes that can be configured for coupling with an implanted medical device or generator in conjunction with sensing, stimulation and/or neuromodulation within a biological application.

BACKGROUND

In some embodiments, ring electrodes are provided on the distal end of a lead for sensing and/or stimulation within a human body. The distal end of a lead is placed adjacent tissue that is to be sensed or stimulated and the ring electrodes either transmit or receive energy. In some cases, it is useful to have very discrete locations energized, and accordingly, use only a segment of a ring electrode, rather than the entire ring. Manufacturing discrete electrode segments can be difficult, particularly where multiple electrode segments are desired on a small diameter lead. In addition, it can be very difficult to overmold these leads with very small dimensions. For these and other reasons, there is a need for the invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Figure 1:
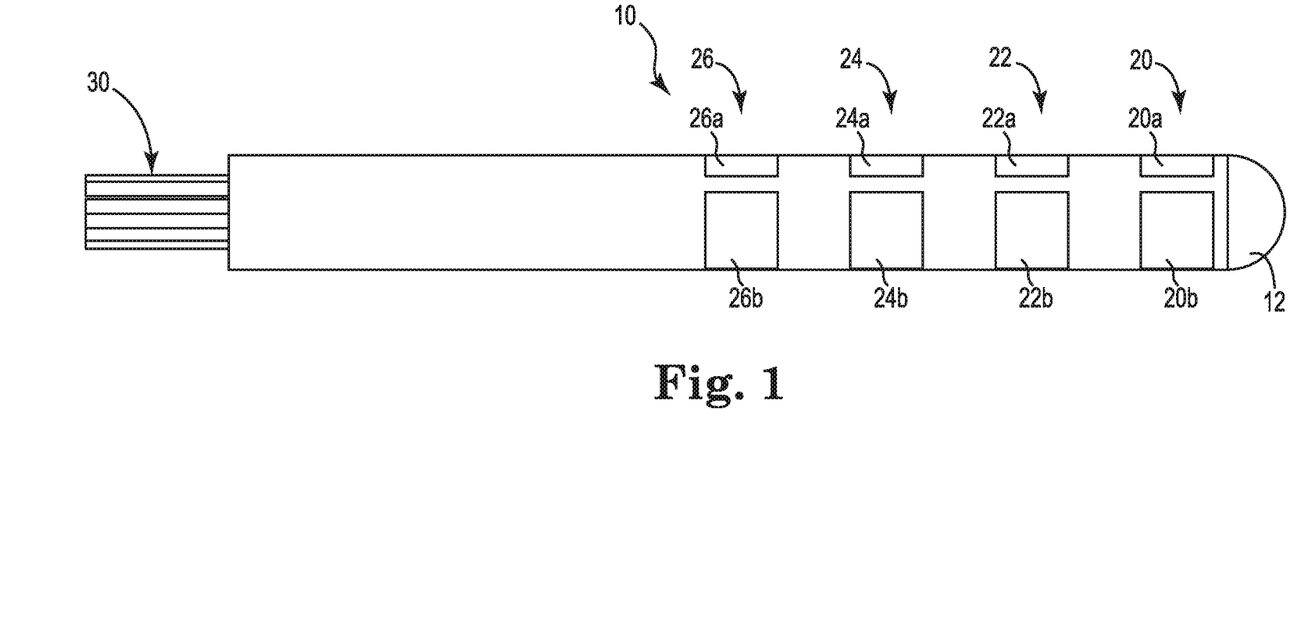
FIG. 1 illustrates a perspective view of a medical lead with segmented electrodes in accordance with one embodiment.

FIG. 1 illustrates a perspective view of a medical lead 10 in accordance with one embodiment. In one embodiment, lead 10 includes, adjacent its distal end 12, four electrodes 20, 22, 24, 26. In other embodiments, more or less electrodes may be included. In one embodiment, each of electrodes 20, 22, 24, 26 is segmented, such that each has a plurality of individually accessible electrode segments. In one embodiment, first electrode 20 includes first, second, and third electrode segments 20a, 20b, and 20c; second electrode 22 includes first, second, and third electrode segments 22a, 22b, and 22c; third electrode 24 includes first, second, and third electrode segments 24a, 24b, and 24c; and fourth electrode 26 includes first, second, and third electrode segments 26a, 26b, and 26c. In one embodiment, each electrode segment a/b/c of each electrode 20, 22, 24, 26 extend radially about the outer diameter of lead 10, which is essentially an extended cylindrical shape in one embodiment, and each electrode segment a/b/c of each electrode 20, 22, 24, 26 are located along the same axial length of lead 10. Because the electrode segments are spaced radially about the circumference of lead 10, only some of the segments are visible in the side view of FIG. 1.

In various other embodiments, there can be any number of combinations of electrodes and electrode segments. For example, there can be two, three, four or five electrode segments for each of electrodes 20, 22, 24, 26. In some embodiments, some of the electrodes are single ring electrodes, without segmentation, while other of the electrodes are segmented in various combinations two, three, four or five or more segments. In some embodiments, less than four electrodes are used, and in others more than four are used. Also, the length of the electrode segments can be varied. In the illustration, each electrode segment has the same axial and radial length, but in other embodiments the relative axial and/or radial length of each can vary.

In operation, lead 10 may be configured for use within a human body, such as within the vasculature. Once within a human body, each of electrode segments 20*a/b/c*, 22*a/b/c*, 24*a/b/c*, 26*a/b/c* may be used for directional stimulation or for positional feedback sensing. In one embodiment, rather than using a single ring electrode that spans the entire 360° circumference of the lead, lead 10 includes electrode segments 20*a/b/c*, 22*a/b/c*, 24*a/b/c*, 26*a/b/c*, which only span a portion of the circumference of lead 10 (for example, 180°, 120°, 90° degrees or less), such that directional stimulation or positional feedback sensing can be much more precisely controlled relative to a given target within the human body.

A plurality of conductors 30 are illustrated extending from lead 10. Each electrode segment 20*a/b/c*, 22*a/b/c*, 24*a/b/c*, 26*a/b/c* has a single corresponding conductor within the plurality of conductors 30, and each are electrically isolated from each other. The plurality of conductors 30 are available at the proximal end of lead 10 such that each of the 12 electrode segments 20*a/b/c*, 22*a/b/c*, 24*a/b/c*, 26*a/b/c* are electrically accessible at the proximal end of lead 10 via one conductor of the plurality of conductors 30.

Medical lead 10 in accordance with embodiments described herein, allow for the manufacture of leads having increased density of electrode segments. Increased density of electrode segments is useful in a variety of applications. For example, lead 10 can be used in deep brain stimulation (DBS), in which lead 10 delivers electrical pulses into one or several specific sites within the brain of a patient to treat various neurological disorders, such as chronic pain, tremors, Parkinson's disease, dystonia, epilepsy, depression, obsessive-compulsive disorder, and other disorders. In other applications, lead 10 may be configured for spinal cord stimulation, peripheral nerve stimulation, dorsal root stimulation, cortical stimulation, ablation therapies, cardiac rhythm management leads, various catheter configurations for sensing, and various other therapies where directional sensing or stimulation are needed.

Figure 2:
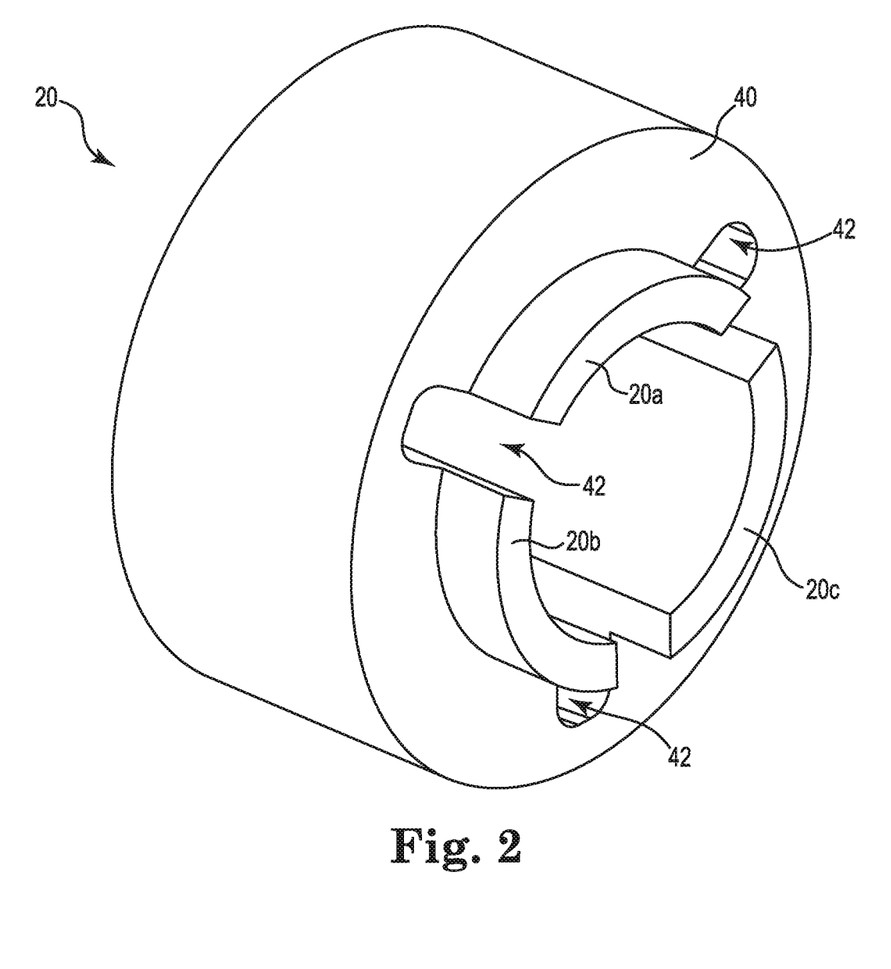
FIG. 2 illustrates a perspective view of a non-ground segmented electrode for manufacturing a lead in accordance with one embodiment.
Figure 3:
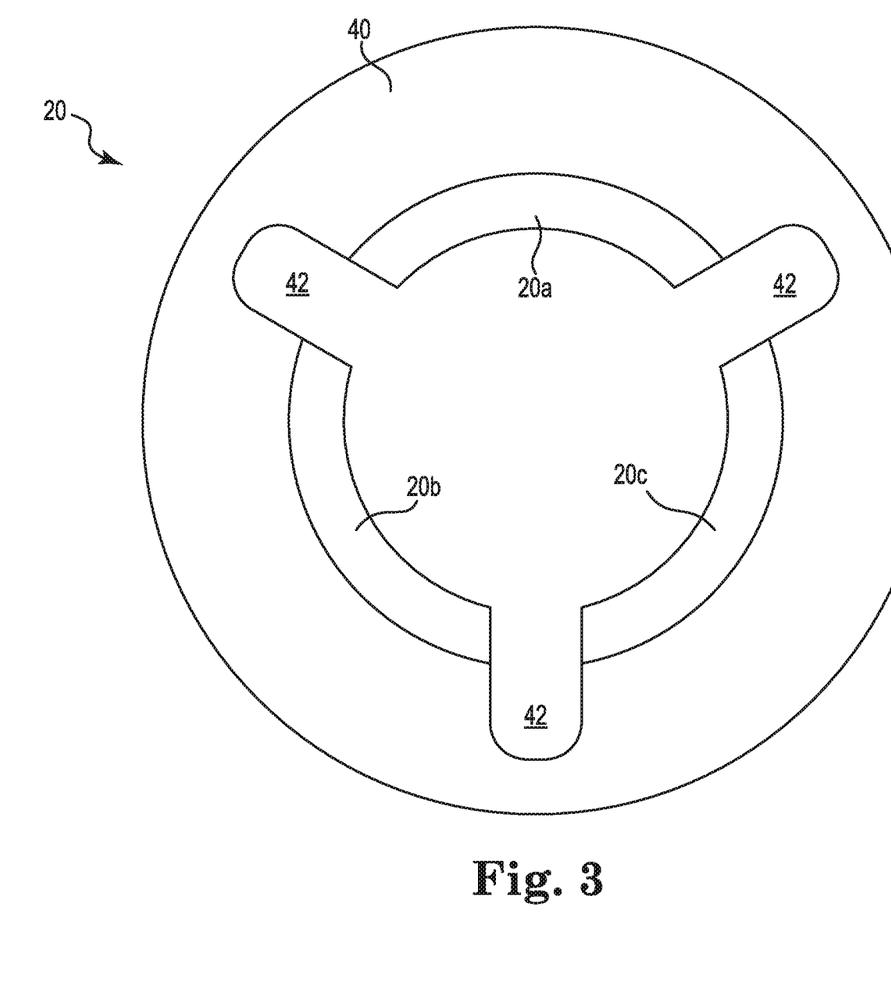
FIG. 3 illustrates a front view of a non-ground segmented electrode for manufacturing a lead in accordance with one embodiment.
Figure 4:
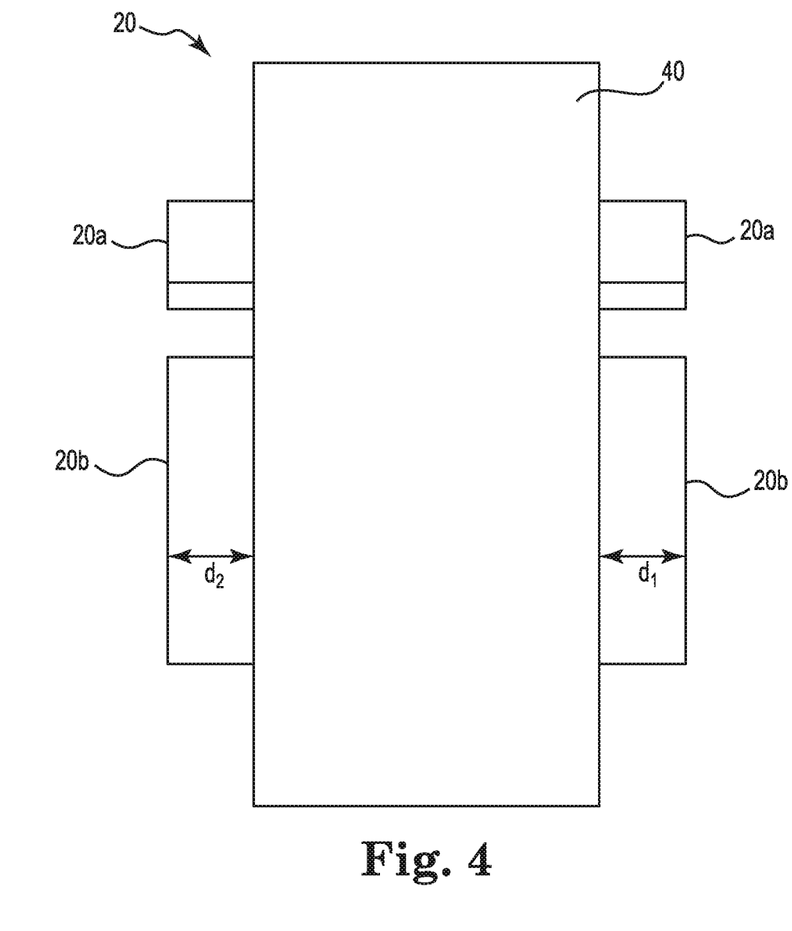
FIG. 4 illustrates a side view of a non-ground segmented electrode for manufacturing a lead in accordance with one embodiment.

FIGS. 2-4 illustrate non-ground electrode 20 in perspective, front and side views, respectively, in accordance with one embodiment. In one embodiment, the manufacture of lead 10 begins with a non-ground electrode, such as electrode 20, which includes electrode segments 20*a/b/c* and an electrode body 40. Electrode body 40 is provided with slots 42, which in one embodiment are spaced apart by approximately 120 degrees, such that each of electrode segments 20*a/b/c* are spaced from each other by a slot 42, as best illustrated in FIG. 3. Once electrode body 40 is ground down from its outer perimeter down into slots 42, each of electrode segments 20*a/b/c* will be independently defined and can be readily electrically isolated from each other. This description of electrode 20 is similarly applicable to the configuration of electrodes 22, 24 and 26.

In FIGS. 2-4, three electrode segments 20*a/b/c* are illustrated separated by about 120 degrees, but in other embodiments, a different amount of segments, such as two or four, can be used. Although the electrode segments are illustrated substantially equally sized and spaced, in other embodiments some segments can be smaller than others and some may be grouped closer together. For example, if four electrode segments are used, four slots are provided spaced apart by 90°. Also, in some embodiments, it may be desirable to have one radially longer electrode segment with two radially shorter segments. In one such embodiment, two slots can be separated by 120°, while the others are separated by 90°. Any number of combinations in various embodiments are possible.

In one embodiment, each of electrode segments 20*a/b/c* extend outward from electrode body 40 on both sides, as best illustrated in FIG. 4. In one embodiment, electrode segments 20*a/b/c* extend outward a distance $d_1$ on a first side of electrode 20 and electrode segments 20*a/b/c* extend outward a distance $d_2$ on an opposite second side of electrode 20. In one embodiment, distances $d_1$ and $d_2$ are the same, and in other embodiments, they are different. Configuring electrode segments 20*a/b/c* with these longer section can help facilitate coupling conductors and accommodating overmolded material, as will be further explained below.

Figure 5:
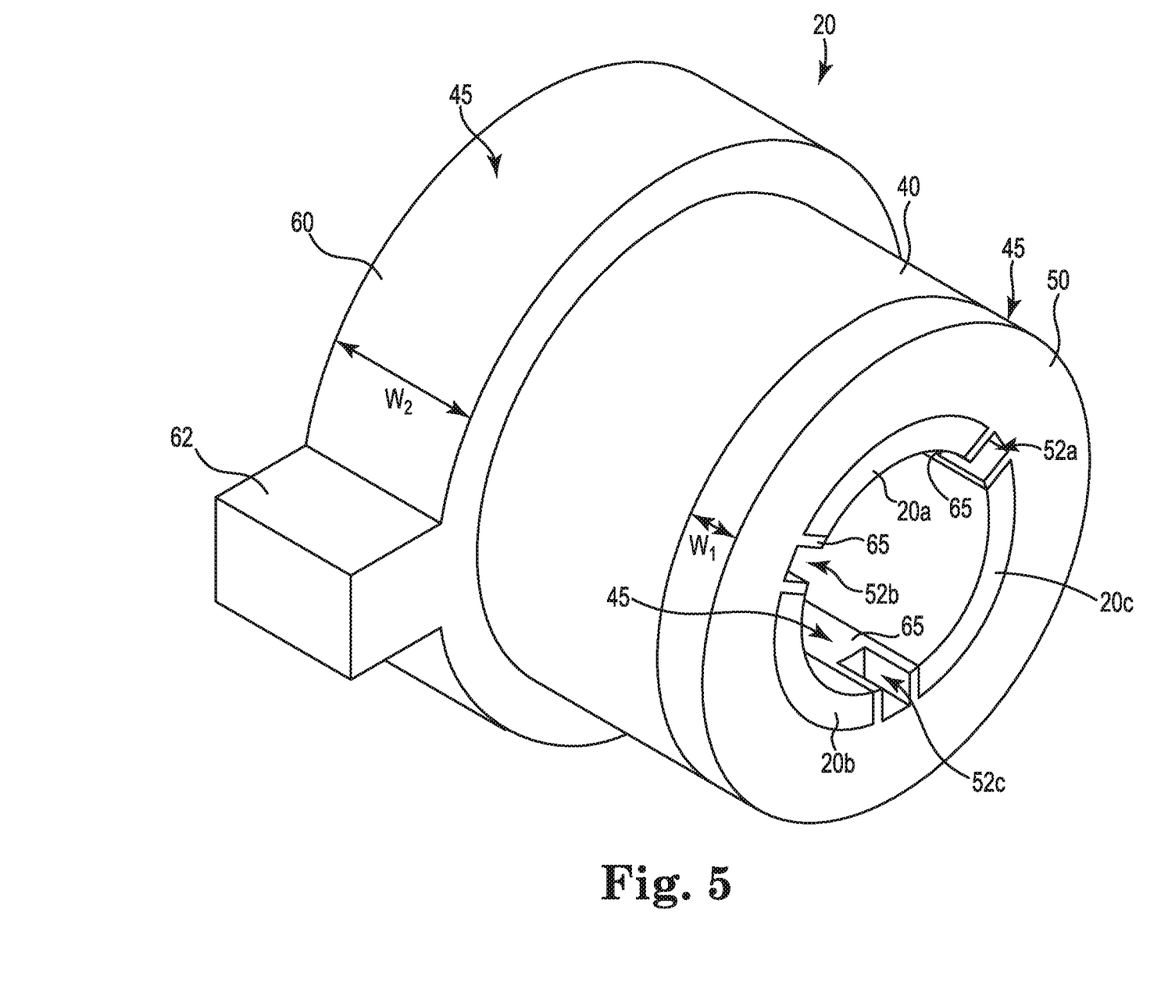
FIG. 5 illustrates a perspective view of an overmolded, non-ground segmented electrode for manufacturing a lead in accordance with one embodiment.
Figure 6:
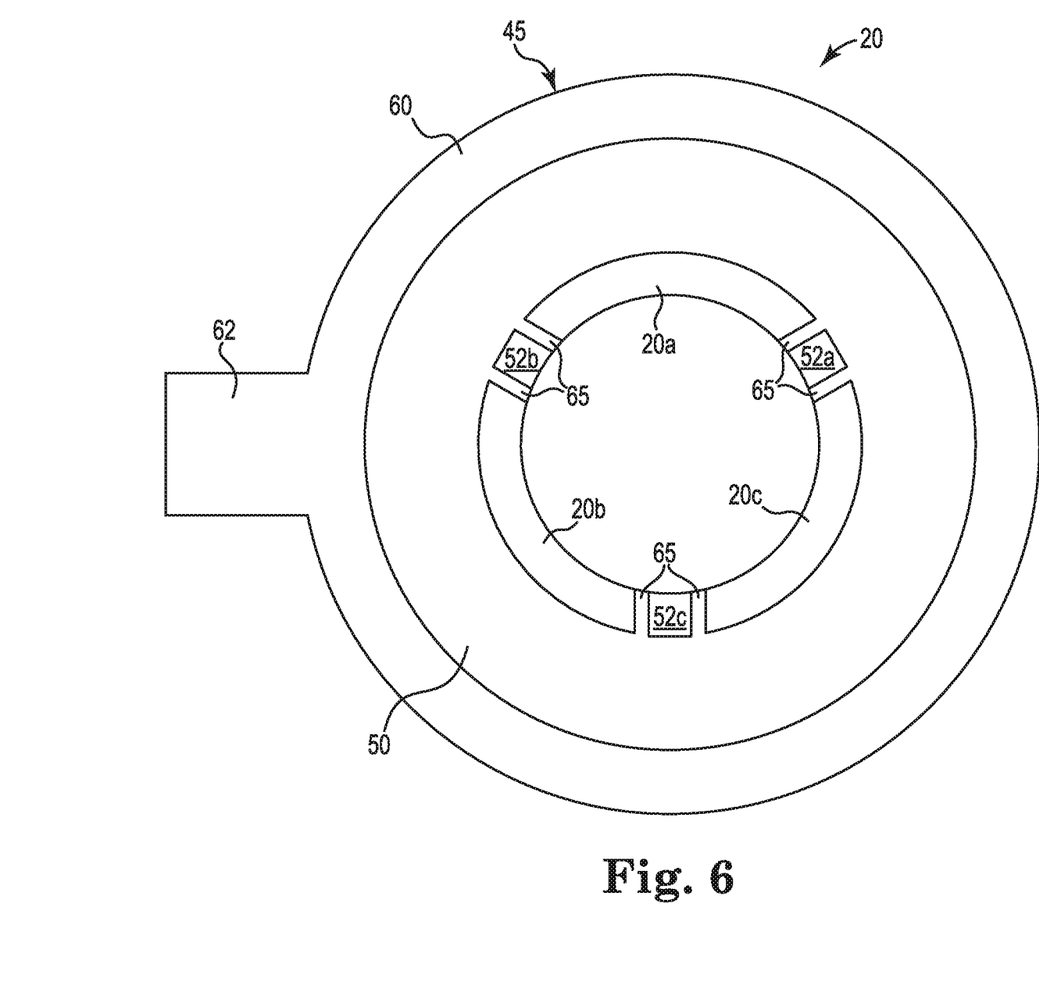
FIG. 6 illustrates a front view of an overmolded, non-ground segmented electrode for manufacturing a lead in accordance with one embodiment.
Figure 7:
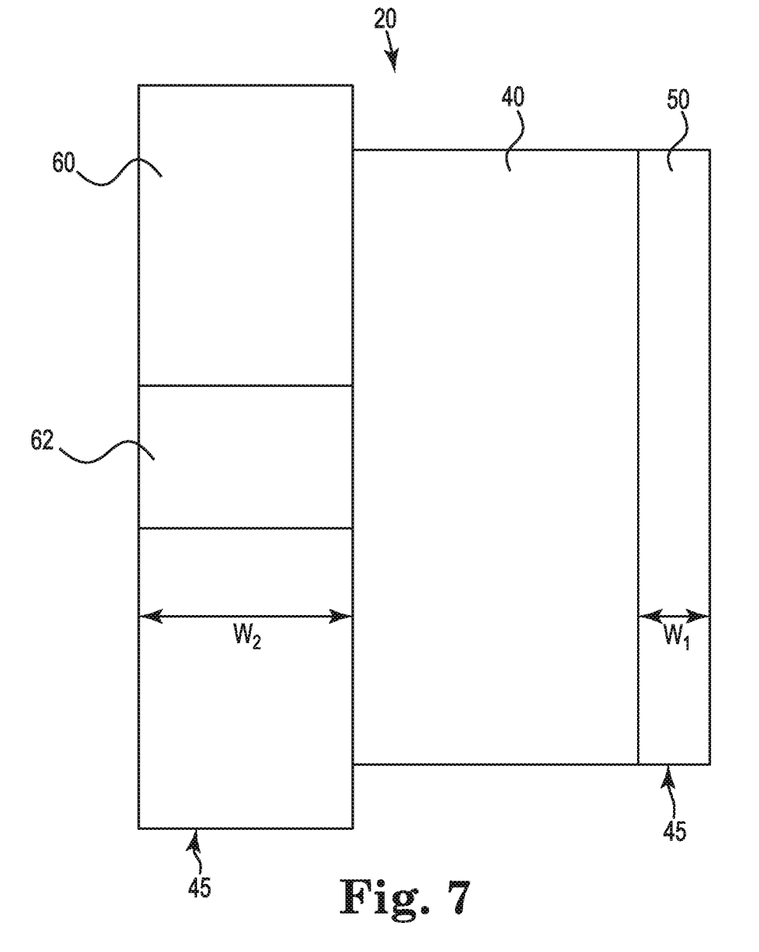
FIG. 7 illustrates a side view of an overmolded, non-ground segmented electrode for manufacturing a lead in accordance with one embodiment.

FIGS. 5-7 illustrate non-ground electrode 20 with overmold portions 45 in perspective, front and side views, respectively, in accordance with one embodiment. In one embodiment, non-ground electrode 20 is overmolded with a plastic or similar polymer material in three main portions relative to non-ground electrode 20. In one embodiment, overmold portions 45 include first overmold portion 50, second overmold portion 60, and third overmold portions 65.

In one embodiment, first overmold portion 50 is molded over the section of electrode segments 20*a/b/c* that extends out from electrode body 40 a distance $w_1$ on a first side of electrode 20. In one embodiment, the distance $w_1$ that first overmold portion 50 extends out from electrode body 40 is the same as the distance $d_1$ that electrode segments 20*a/b/c* extend out from electrode body 40, such that they are substantially flush on a first side of electrode 20. In one embodiment, first overmold portion 50 also has an outer diameter that is substantially the same as the outer diameter of electrode body 40 such that they are substantially flush on the outer diameter. In other embodiments, these respective dimensions can be different.

In one embodiment, second overmold portion 60 is molded over the section of electrode segments 20*a/b/c* that extends out from electrode body 40 a distance $w_2$ on a on a second side, opposite the first side. In one embodiment, the distance $w_2$ that second overmold portion 60 extends out from electrode body 40 is greater than the distance $d_2$ that electrode segments 20*a/b/c* extend out from electrode body 40, such electrode segments 20*a/b/c* are recessed relative to second overmold portion 60 (best seen in FIG. 8). In one embodiment, second overmold portion 60 has an outer diameter that is slightly larger than the outer diameter of electrode body 40. In one embodiment, second overmold portion 60 further includes tab 62 extending out from its outer diameter.

In one embodiment, third overmold portions 65 substantially fill slots 42 between each of electrode segments 20*a/b/c*, extending between first and second overmold portions 50 and 60. In one embodiment, although third overmold portions 65 substantially fill slots 42, none of third overmold portions 65, nor any of overmold portions 45, cover the inner surfaces 21 of electrode segments 20*a/b/c*. Accordingly, these inner surfaces 21 of electrode segments 20*a/b/c* are readily able to accept conductor, as will be explained further, since they are free of overmold portions 45 or any molded or insulative material.

In one embodiment, each of third overmold portions 65 further include keys 52, for example, the third overmold portion 65 between first and second electrode segments 20*a* and 20*b* includes key 52*b*, the third overmold portion 65 between second and third electrode segments 20*b* and 20*c* includes key 52*c*, and third overmold portion 65 between third and first electrode segments 20*c* and 20*a* includes key 52*a*. In one embodiment, keys 52*a/b/c* can be useful in the assembly of medical lead 10.

In one embodiment, when overmold portions 45 are added over non-ground electrode 20, each of keys 52*a/b/c* is precisely located relative to tab 62. For example, in FIG. 5, if it is assumed that tab 62 is illustrated at 0 degrees on the circular radius of electrode 20, first key 52*a* is approximately 30 degrees advanced from 0 degrees, second key 52*b* is approximately 150 degrees advanced from 0 degrees, and third key 52*c* is approximately 270 degrees advanced from 0 degrees. In this way, knowing the relative radial location of tab 62 also verifies the relative radial location of each of keys 52*a/b/c*. This is very useful in the process of attaching the plurality of conductors 30 to the electrode segments 20*a/b/c* for each of the electrodes. Where several or more electrodes are used in a lead, and where these electrodes each have a plurality of electrode segments, ensuring that each conductor is coupled to just one electrode segment and does not interfere with other conductors becomes quite challenging, especially when there are a large number of conductors within a very small diameter lead 10. Using the location of the keys 52 relative to the tabs 62 is useful where multiple electrodes are assembled together.

Figure 8:
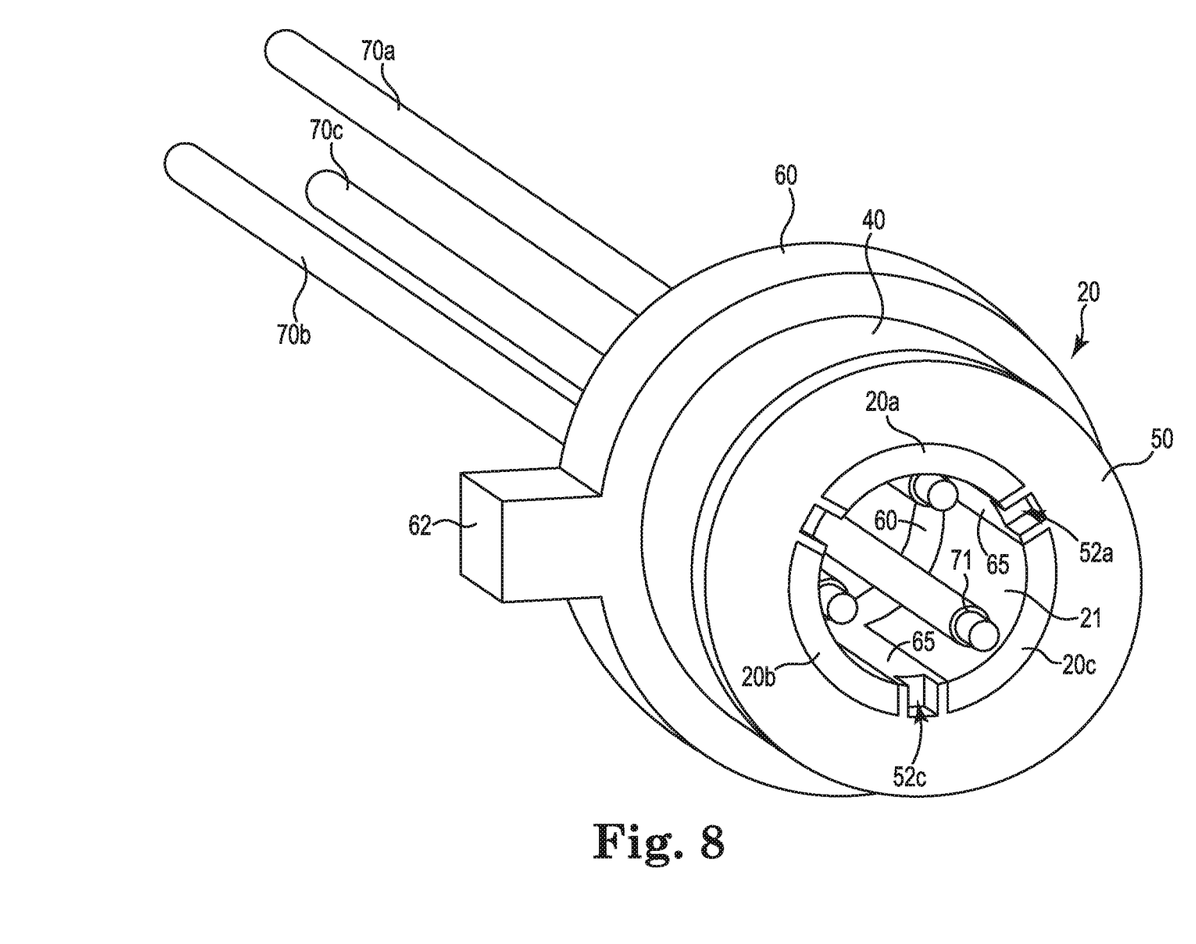
FIG. 8 illustrates a perspective view of an overmolded, non-ground segmented electrode coupled with conductors for manufacturing a lead in accordance with one embodiment.

FIG. 8 illustrates a partially assembled electrode 20 in accordance with one embodiment. In one embodiment, three conductors 70*a*, 70*b* and 70*c*, from the plurality of conductors 30, are illustrated coupled to non-ground electrode 20. Specifically, first conductor 70*a* is coupled to an inner surface 21 of first electrode segment 20*a*, second conductor 70*b* is coupled to an inner surface 21 of second electrode segment 20*b*, and third conductor 70*c* is coupled to an inner surface 21 of third electrode segment 20*c*. Because each conductor is coupled to only one electrode segment, and each electrode segment is electrically isolated from the others by third overmold portions 65 filling the slots 42 between them, each conductor is electrically coupled to just one specific electrode segment, such that the conductor can independently sense or energize one specific electrode segment.

Conductors 70*a/b/c* can be attached to electrode segments 20*a/b/c* in a variety of ways, including welding, soldering, bonding, and gluing. In one embodiment, each of the conductors 70*a/b/c* have an insulative cover 71. When conductors 70*a/b/c* are coupled to electrode segments 20*a/b/c*, the cover portion is removed at the location of the electrode inner surface 21. In the case where the conductors are welded, the cover 71 is melted away in the process, thereby electrically coupling the conductor and electrode segment. Because the conductors are coupled to each of the electrodes individually, there are no blind welds, such that there are line of sight welds that are readily inspectable, which will ensure more quality welds of the conductors.

In one embodiment, each conductor is attached to a specific location within an electrode segment in order to accommodate the plurality of conductors within medical lead 10 when a plurality of electrodes are used. For example, each conductor can be radially offset relative to each other conductor so no conductor interferes with another. Because of the combination of the keys 52 and tabs 62 of the overmold portions 45, these locations can be readily identified and controlled in the manufacturing process.

Figure 9:
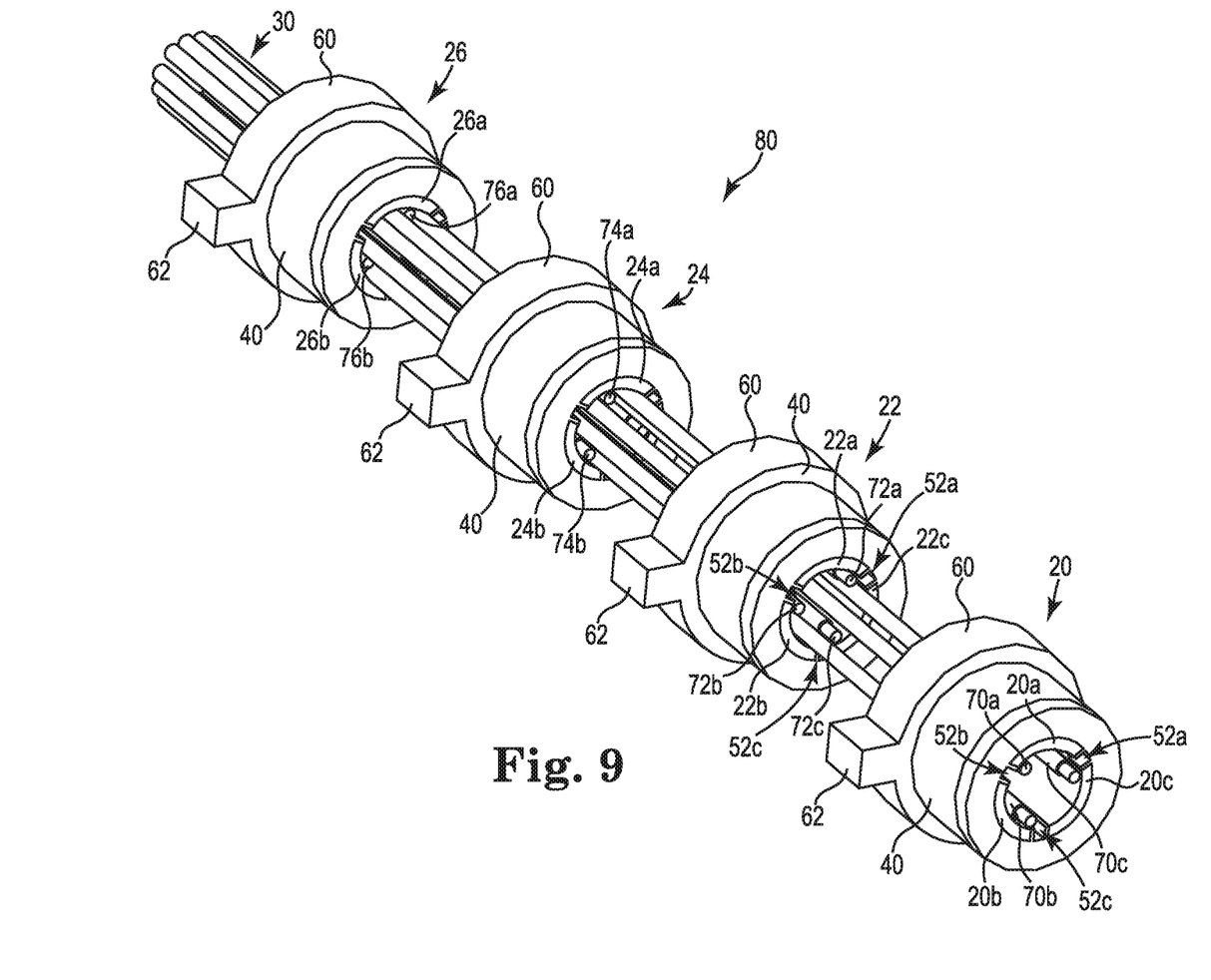
FIG. 9 illustrates an exploded perspective view of a plurality of overmolded, non-ground segmented electrode coupled with conductors for manufacturing a lead in accordance with one embodiment.

FIG. 9 illustrates electrode assembly 80 in accordance with one embodiment. Electrode assembly 80 in FIG. 9 is illustrated in an exploded form to illustrate some of the inner aspect features. In one embodiment, electrode assembly 80 includes first through fourth non-ground electrodes 20/22/24/26. In one embodiment, each of non-ground electrodes 20/22/24/26 are formed similar to that described above for electrode 20, such that each have electrode segments a/b/c and each have overmold portions 45 added. In other embodiments, electrode assembly 80 can include more or less non-ground electrodes, such as two, three, five or six. Also, each of the included non-ground electrodes can have the same number of segments or can have differing numbers of segments. For example, three non-ground electrodes may be included electrode assembly 80, a first having two electrode segments, a second having three electrode segments, and a third having four electrode segments, and at least one having overmold portions 45.

In one embodiment, each of non-ground electrodes 20/22/24/26 include first through third electrode segments a/b/c. One of the plurality of conductors 30 is attached to one (and only one) of the electrode segments, such that there are 12 conductors in the plurality of conductors 30, one for each of the electrode segments of each electrode. Because of the relatively large number of conductors that must fit into the relatively small diameter of non-ground electrodes 20/22/24/26, the radial attachment location of each conductor to a corresponding electrode segment should be coordinated to minimize interference and crowding between them.

In one embodiment, conductors 70*a/b/c* are coupled to first non-ground electrode 20. First conductor 70*a* is coupled to an inner surface of first electrode segment 20*a* at a location that is immediately adjacent second key 52*b*. Similarly, second conductor 70*b* is coupled to an inner surface of second electrode segment 20*b* at a location that is immediately adjacent third key 52*c*. Third conductor 70*c* is then coupled to an inner surface of third electrode segment 20*c* at a location that is immediately adjacent first key 52*a*.

In order to facilitate good spacing and avoid crowding of the conductors, conductors 72*a/b/c* are coupled to second non-ground electrode 22 at different relative radial locations. Specifically, fourth conductor 72*a* is coupled to an inner surface of first electrode segment 22*a* at a location that is immediately adjacent first key 52*a*. Fifth conductor 72*b* is coupled to an inner surface of second electrode segment 22*b* at a location that is immediately adjacent second key 52*b*. Sixth conductor 72*c* is then coupled to an inner surface of third electrode segment 22*c* at a location that is immediately adjacent third key 52*c*. As such, each of fourth-sixth conductors 72*a/b/c* are radially offset relative to each of first-third conductors 70*a/b/c*, such that the conductors will not interfere with each other as they pass from one end of the assembly 80 to the other end.

Seventh-ninth conductors 74*a/b/c* and tenth-twelfth conductors 76*a/b/c* are similarly radially offset (radially between conductors 70*a/b/c* and conductors 72*a/b/c* in one embodiment) and respectively coupled to electrode segments 24*a/b/c* of third non-ground electrode 24 and electrode segments 26*a/b/c* of fourth non-ground electrode 26. Accordingly, all 12 of the plurality of conductors 70*a/b/c*, 72*a/b/c*, 74*a/b/c* and 76*a/b/c* are radially offset relative to each other such that all 12 conductors will not crowd or interfere with each other as they pass from one end of the electrode assembly 80 to the other end.

Because the fixed relative radial location of keys 52*a/b/c* and tab 62 on each of first-fourth non-ground electrodes are known, this has advantages in the process of coupling each of the plurality of conductors 30 to the non-ground electrodes 20-26. For example, during assembly, each of tabs 62 can be placed into respective recesses of an assembly fixture such that the non-ground electrodes 20-26 cannot rotate during assembly. Similarly, keys 52a/b/c can have tabs from the assembly fixture secured into them such that their relative radial location is known to the assembly fixture. In this way, each of the plurality of conductors 30 can be readily located at the appropriate radial location relative to each of the respective electrode segments so that none of the plurality of conductors 30 interfere with each other within the small diameter within each of the electrodes 20/22/24/26. Because of the known fixed relative radial location of tabs 62 and keys 52, the attachment of the conductors to the electrodes is highly repeatable and precise.

In one embodiment, each of electrodes 20/22/24/26 have respective conductors attached and then the electrodes with attached conductors are assembled together. For example, FIG. 8 illustrates conductors 70a/b/c respectively connected to electrode segments 20a/b/c of electrode 20, and similarly conductors 72a/b/c are respectively connected to electrode segments 22a/b/c of electrode 22, conductors 74a/b/c are respectively connected to electrode segments 24a/b/c of electrode 24, and conductors 76a/b/c are respectively connected to electrode segments 26a/b/c of electrode 26. Then, the electrodes 20/22/24/26 with attached conductors are assemble together, much like shown in FIG. 9. Because the tabs 62 and respective keys 52 are appropriately aligned, in one embodiment, aligning each of the tabs will ensure the conductors are in the appropriate radial alignment.

Figure 10:
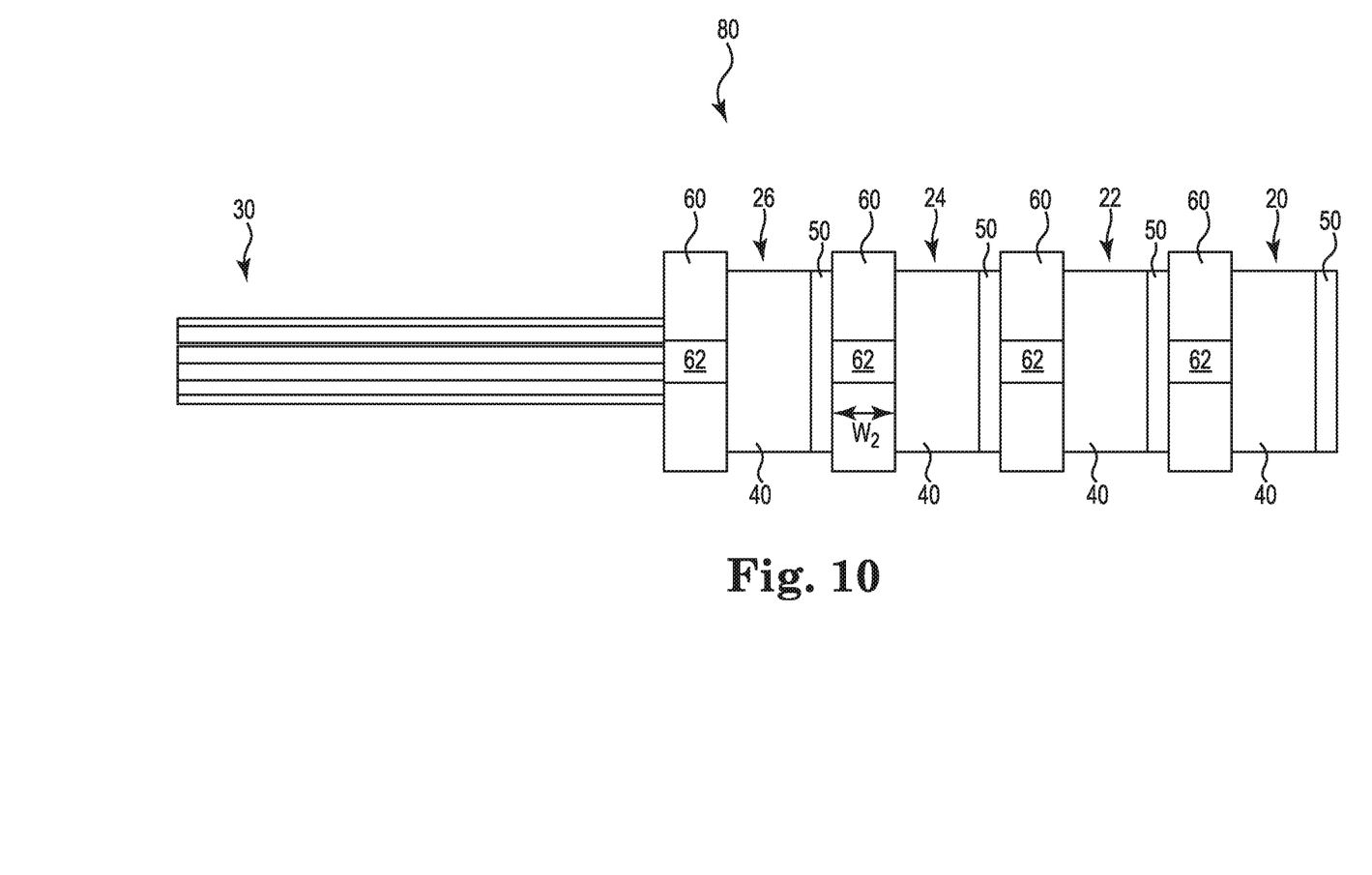
FIG. 10 illustrates a perspective view of a plurality of overmolded, non-ground segmented electrode coupled with conductors for manufacturing a lead in accordance with one embodiment.

FIG. 10 illustrates electrode assembly 80 in accordance with one embodiment. Electrode assembly 80 in FIG. 10 is illustrated in an assembled form after each of the plurality of conductors 30 have been coupled to a respective electrode segment and each of the electrodes 20/22/24/26 are assembled together. In one embodiment, the distance $w_2$ that second overmold portion 60 extends out from each respective electrode body 40 is controlled in order to create the desired axial distance between each electrode 20/22/24/26. In various applications, the axial distance between the electrodes and/or electrode segments is tailored to the particular application depending upon, for example, what tissue is being stimulated or sensed. By adjusting the distance $w_2$ of second overmold portion 60, the precise axial distance between the electrodes 20/22/24/26 is readily controlled in the assembly process.

Once electrode assembly 80 is assembled as illustrated in FIG. 10, the entire assembly is reflowed such that all the connected portions are flowed over with the plastic material of overmold portions 45. The mold material flows into the inner diameter of the electrode assembly 80 and fills any voids between the plurality of conductors 30 and electrodes 20/22/24/26. The amount of molding material needed to effectively fill any gaps in the assembly may vary depending on the relative diameters and number of conductors. Accordingly, the overall diameter of overmold portion 60 can be increased or decreased as needed to ensure that the correct volume of molding material is available during the reflow process to ensure any voids are filled. As noted in with respect to FIG. 6, the outer diameter of second overmold portion 60 is independent of the electrode body diameter 40, and is instead determined by the amount of molding material that is needed for filling the gaps and inner diameter of the electrode assembly 80. In one embodiment, once tabs 62 are aligned in the electrode assembly 80, tabs 62 are removed prior to reflow in order to provide a more uniform distribution of molding material during the reflow. Electrode assembly 80 can be reflowed in any of a variety of ways, such as a heat shrink tubing process or by heating within a die cavity.

Once the reflow is complete, the part is ground down to a finished diameter such that lead 10 illustrated in FIG. 1 is produced. Such a grinding process can be, for example, a centerless grinding process where the electrode body 40 of each electrodes 20/22/24/26, along with the reflowed molding material on the outer diameter, is ground away from the external diameter of electrode assembly 80 inward until slots 42 are exposed on the outer lead diameter, thereby producing the electrode segments a/b/c for each of electrodes 20/22/24/26 on the outer diameter of medial lead 10.

Manufacturing medical lead 10 to produce segmented electrodes using overmold portions with tabs and keys achieves an electrode array on a small diameter lead. In one embodiment, this creates a lead 10 having twelve discrete channels, which is not easily obtained with conventional techniques.

In one embodiment, using overmold portions with tabs and keys achieves decreased outer diameters of lead 10. In one embodiment, a lead made with this process is sized with an outer diameter of 0.031 inches, making it appropriate for small animal or pediatric applications.

Figure 11:
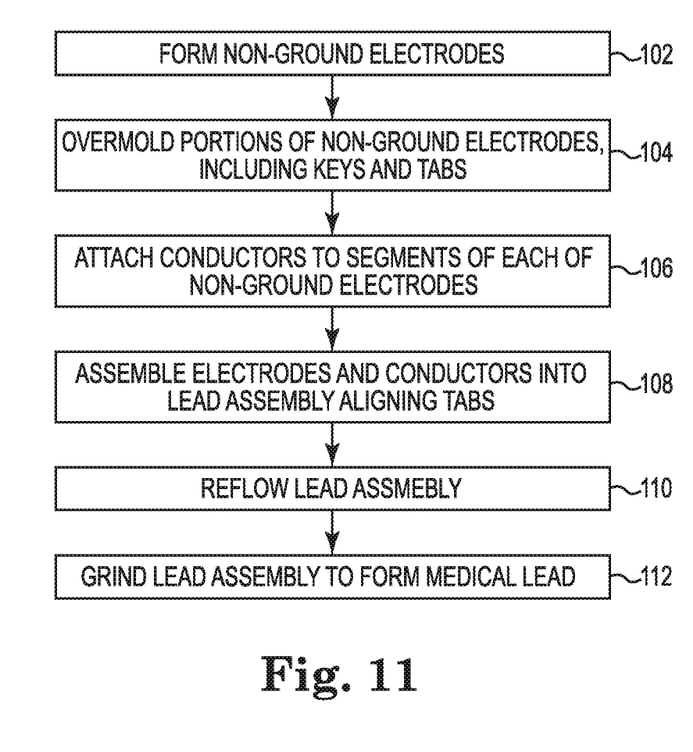
FIG. 11 illustrates a method of forming a medical lead with segmented electrodes in accordance with one embodiment.

FIG. 11 illustrates a method of forming a segmented electrode lead, such as medical lead 10, in accordance with one embodiment. First, at step 102, non-ground electrodes are formed. In one embodiment, multiple non-ground electrodes, such as non-ground electrode 20 of FIGS. 2-4 are formed. In various embodiments, one, two, three, four or more non-ground electrodes are formed. At step 104, overmold portions are added to at least one of the formed non-ground electrodes. In one embodiment, the overmold portions include keys and tabs, such as the overmold portions 45 of FIGS. 5-7. In one embodiment, the keys and tabs are located at specific relative radial locations that are known.

At step 106 one conductor from a plurality of conductors are attached to one segment of the non-ground electrodes. In one embodiment, there are a plurality of non-ground electrodes, and each have a plurality of segments. One conductor is coupled to one segment, such as illustrated in FIG. 8. In one embodiment, conductors are coupled at specific radial locations of each electrode segment by using the known radial locations of either keys or tabs or both.

At step 108, electrodes and conductors are assembled into an electrode or lead assembly and tabs are aligned, such as illustrated in FIGS. 9 and 10. In one embodiment, the axial distance between adjacent electrodes is determined by the width of the overmolded portion. Once the electrodes are assembled, at step 110 the electrode or lead assembly is reflowed, such that the overmolded material is flowed into the inner diameter of the electrode assembly and fills any voids between the plurality of conductors and electrodes. At step 112, the reflowed assembly is then ground into medical lead 10, such as illustrated in FIG. 1. In one embodiment, a centerless grinding process is used to grind down the outer diameter of the assembly until the electrodes are separated into electrode segments.

Although specific embodiments have been illustrated and described herein, it will be appreciated by those of ordinary skill in the art that a variety of alternate and/or equivalent implementations may be substituted for the specific embodiments shown and described without departing from the scope of the invention. This application is intended to cover any adaptations or variations of the specific embodiments discussed herein. Therefore, it is intended that this invention be limited only by the claims and the equivalents thereof

What is claimed is:

1. An electrode assembly for making an electrode lead, the electrode assembly comprising:
   a plurality of non-ground electrodes, at least one non-ground electrode having a plurality of electrode segments;
   overmold portions on the at least one of the plurality of non-ground electrodes, the overmold portions comprising keys and tabs;
   a plurality of conductors, wherein one conductor from the plurality of conductors is coupled to one electrode segment of the at least one non-ground electrode at a location that is based at least in part on the relative radial location of the keys and tabs.

2. The electrode assembly of claim 1, wherein the at least one of the plurality of non-ground electrodes comprise slots thereby defining the plurality of electrode segments between the slots.

3. The electrode assembly of claim 1, wherein the overmold portions comprise a first overmold portion on a first side of the at least one non-ground electrode, a second overmold portion on a second side of the at least one non-ground electrode, opposite the first side, and third overmold portions, which are located between the first and second overmold portions and within the slots in the at least one non-ground electrode.

4. The electrode assembly of claim 3, wherein the second overmold portion comprises at least one tab.

5. The electrode assembly of claim 3, wherein the third overmold portions comprise at least one key.

6. A non-ground electrode for making an electrode lead, the non-ground electrode comprising:
   a plurality of electrode segments defined between a plurality of slots;
   overmold portions on the non-ground electrode, the overmold portions comprising keys and tabs;
   a plurality of conductors, wherein one conductor from the plurality of conductors is coupled to one electrode segment of the non-ground electrode at a location that is based at least in part on the relative radial location of the keys and tabs.

7. The non-ground electrode of claim 6, wherein the overmold portions comprise a first overmold portion on a first side of the non-ground electrode, a second overmold portion on a second side of the non-ground electrode, opposite the first side, and third overmold portions, which are located between the first and second overmold portions and within the slots in the non-ground electrode.

8. The non-ground electrode of claim 7, wherein the second overmold portion comprises at least one tab.

9. The non-ground electrode of claim 7, wherein the third overmold portions comprise at least one key.

* * * * *